(12) United States Patent
Portney

(10) Patent No.: US 7,073,906 B1
(45) Date of Patent: Jul. 11, 2006

(54) ASPHERICAL DIFFRACTIVE OPHTHALMIC LENS

(76) Inventor: Valdemar Portney, 11940 N. Riviera, Tustin, CA (US) 92782

( * ) Notice: Subject to any disclaimer, the term of this patent is extended or adjusted under 35 U.S.C. 154(b) by 0 days.

(21) Appl. No.: 11/273,096

(22) Filed: Nov. 14, 2005

Related U.S. Application Data

(60) Provisional application No. 60/680,411, filed on May 12, 2005.

(51) Int. Cl.
*G02C 7/06* (2006.01)
*G02C 7/04* (2006.01)

(52) U.S. Cl. .................................. 351/168; 351/161
(58) Field of Classification Search .............. 351/156, 351/160 R, 161, 168, 177; 623/4.1–6.64
See application file for complete search history.

(56) References Cited

U.S. PATENT DOCUMENTS 5,229,797 A * 7/1993 Futhey et al. ............... 351/161
5,408,281 A * 4/1995 Zhang ......................... 351/161
6,685,315 B1 * 2/2004 De Carle ..................... 351/161

OTHER PUBLICATIONS

Cohen, Allen Louis, "Diffractive Bifocal Lens Designs," Optometry and Vision Science, vol. 70, No. 6, pp. 461-468, 1993 Americal Academy of Optometry.
Klein, Stanley A., "Understanding the Diffractive Bifocal Contact Lens," Optometry and Vision Science, vol. 70, No. 6, pp. 439-460, 1193 American Academy of Optometry.

* cited by examiner

*Primary Examiner*—Scott J. Sugarman
*Assistant Examiner*—Darryl J. Collins
(74) *Attorney, Agent, or Firm*—Walter A. Hackler

(57) ABSTRACT

A multifocal ophthalmic lens includes a lens element having anterior and posterior surfaces with a central aspherical refractive zone disposed on one of the anterior and posterior surfaces; and a diffractive bifocal zone disposed outside of the aspherical refractive zone. The central aspherical refractive zone may be disposed on the anterior surface and the diffractive bifocal zone may be disposed on the posterior surface.

31 Claims, 6 Drawing Sheets

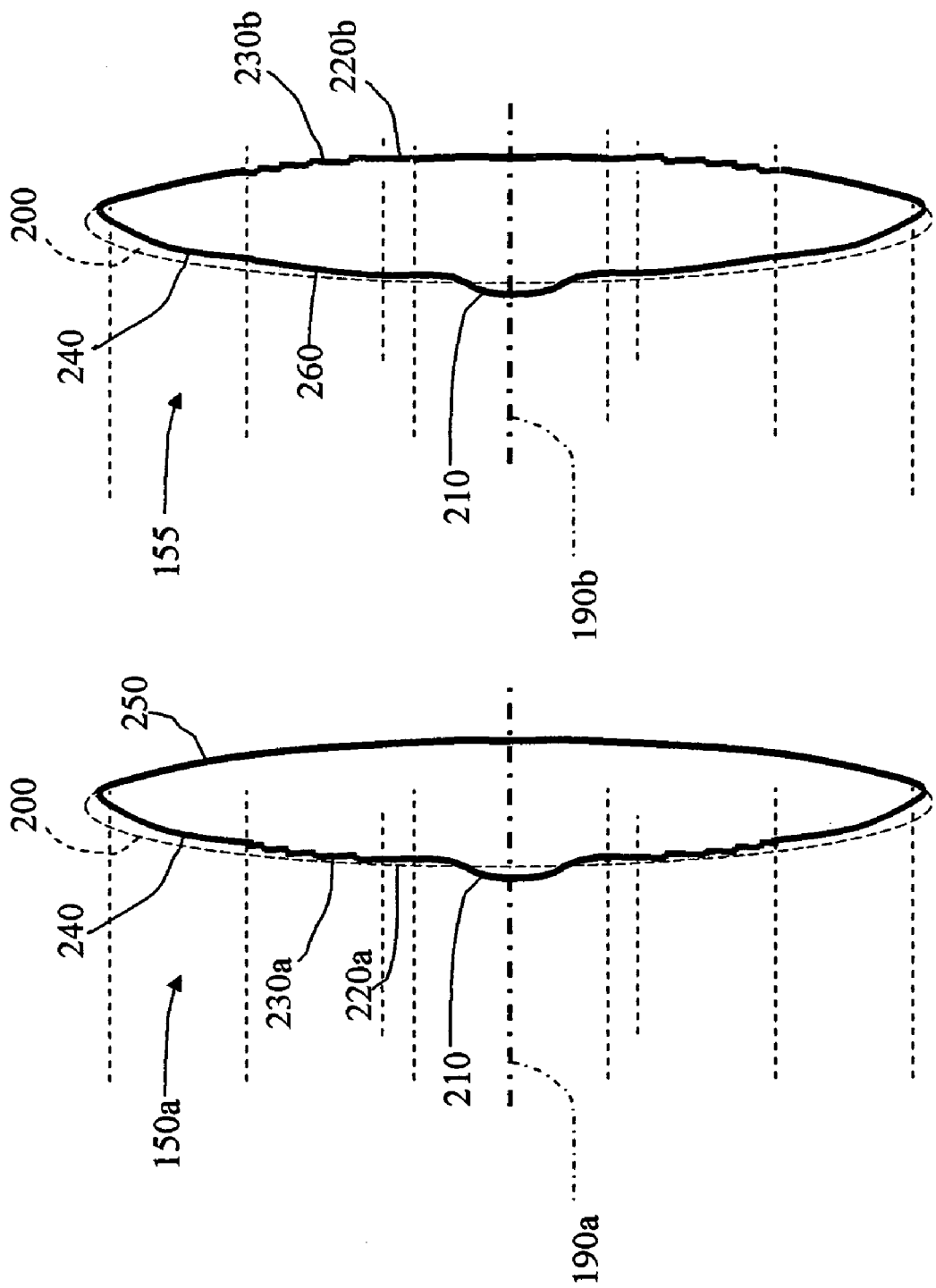

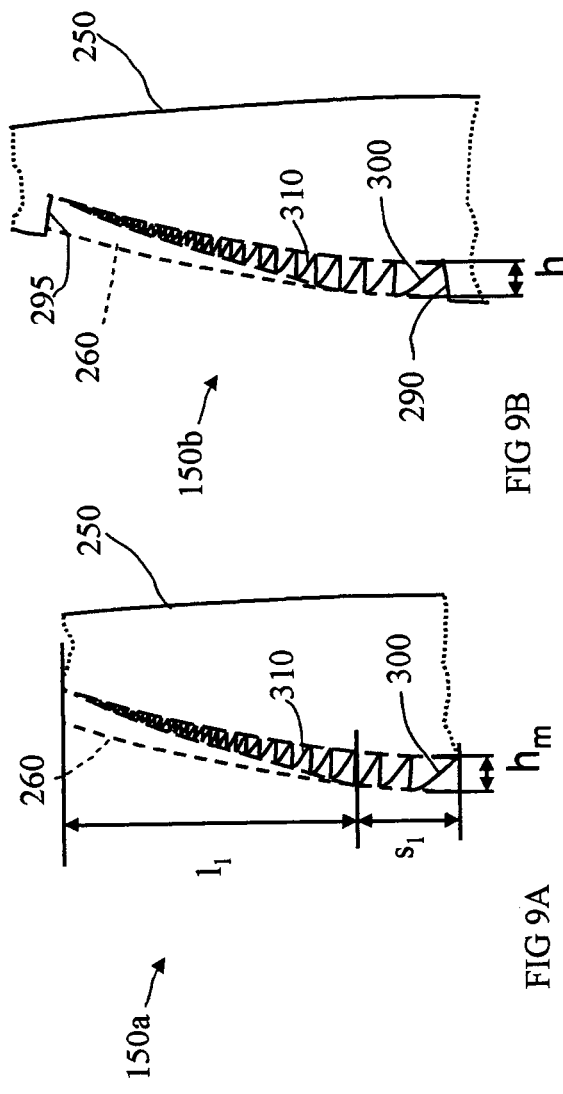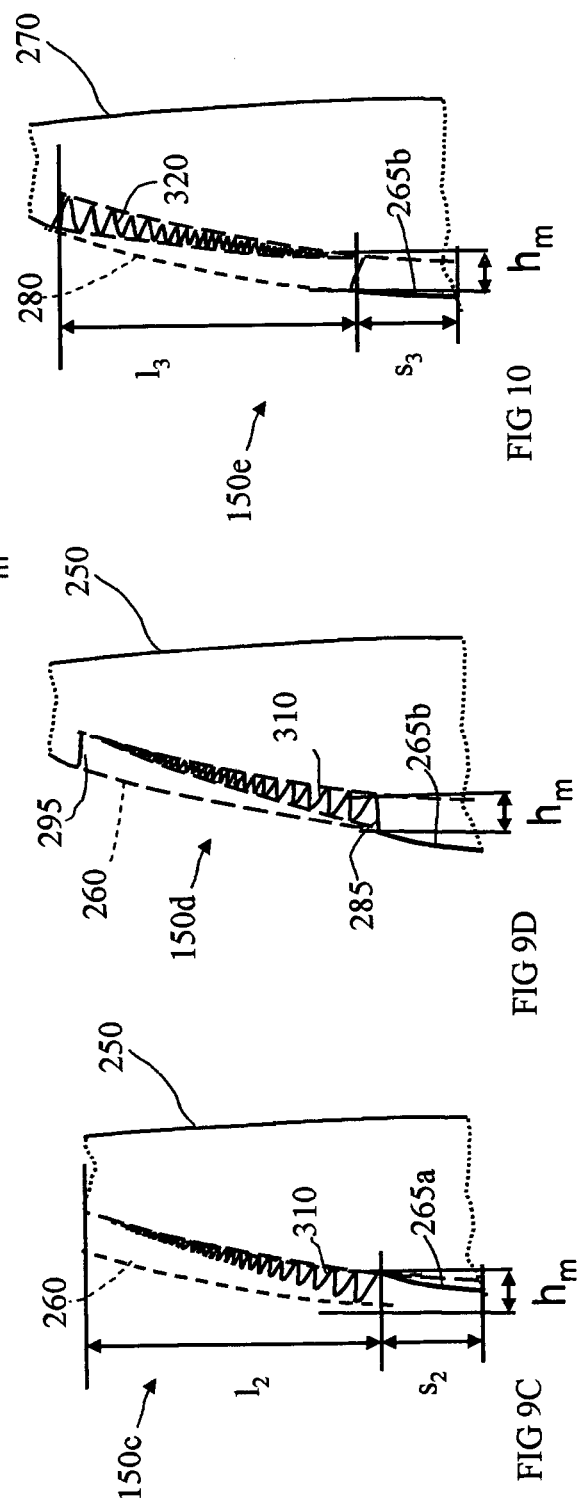

us 7,073,906 B1

ASPHERICAL DIFFRACTIVE OPHTHALMIC LENS

The present application is a continuation of U.S. Ser. No. 60/680,411 filed May 12, 2005. This reference application is to be incorporated in its entirety into the present application.

FIELD OF THE INVENTION

The present invention relates generally to multifocal ophthalmic lenses, and more particularly to multifocal lenses which provide simultaneous refractive and diffractive powers with improved intermediate vision.

BACKGROUND OF THE INVENTION

Ophthalmic lens is defined as a lens suitable for carrying on the eye or inside the eye. Also included are less common vision correction lenses such as artificial corneas and lamellar corneas implants. There is a significant effort to develop a lens for presbyopia correction in a form of refractive or diffractive type lenses.

A fixed single power lens provides good quality of vision but only within the small range of viewing object distances that is usually significantly narrower than the range required for near to distant vision. An improved type of the implant provides a number of powers, so called bifocal or multifocal lens. Reference to bifocal or multifocal terminology is used herein interchangeably. The multifocal ophthalmic lens can provide refractive powers, diffractive powers or a combination of both for required range of vision.

Although refractive lenses were first to be developed they may be interpreted as a specific state of diffractive optics and it may be more appropriate to address a diffractive optic definition in order to describe refractive and diffractive surface types. A diffractive lens that follow the specific rule hereinbelow described. If step sizes are zero or are randomly sized or groove areas are also randomly sized, the lens becomes a refractive type, i.e. the corresponding image locations are defined by Snell's law.

A diffraction lens can be considered as a combination of refractive lens formed by zero step size and phase grating, see FIG. 1. A phase grating can be formed by different types of zone or groove shapes where the blaze shape shown on the FIG. 1 is the most common one. Thus, a blaze shape is cut into a base refractive surface to introduce a phase grating, i.e. a periodic array of optical scattering regions.

Scattering light in all directions by the periodic structure creates constructive and destructive interference of light at different but specific angles depending on wavelength of light which are called diffraction orders. The corresponding wavelength of light used to design the phase grating is called design wavelength.

The directions of the orders and corresponding image locations are defined by the Grating formula, not Snell's law. Zero-order diffractive power coincides with the power of the refractive surface formed by the base curvature and, therefore, loosely called refractive power of the diffractive lens. The key point for the grating to perform, i.e. to form distinct diffraction orders, is to have equal areas of Fresnel zones (grooves) and equal Optical Path Differences between adjacent zones at their borders ($OPD_b$) in the direction of each diffraction order.

According to the wave nature of light, constructive interference of light from different grating regions occurs if light is in phase at the corresponding image plane. The constructive interference would maintain if the light from one of the regions is shifted by the full phase equaled to integer number of the design wavelength. For instance, zero order corresponds to the original direction of the light produced by the refractive base curve, i.e. zero phase shift between light coming from each adjacent blaze zone, $1^{st}$ order is produced by the phase of one wavelength shift between each adjacent blaze, $2^{nd}$ order is produced by the phase of two wavelengths shift between each adjacent blaze and so on. Grating period or blaze zone spacing determines an angle of the given diffractive order, i.e. the corresponding focal length or diffractive power of the given diffraction order.

By the definition of the diffraction order, light can only be channeled along the diffraction orders of the diffractive lens, i.e. discrete channels, but the percent of totally available light that is actually channeled for a given diffraction order depends upon the light phase shift introduced by each blaze zone, i.e blaze material thickness (h), see FIG. 1. The percent of total light at a given order is called diffraction efficiency of this order. In general terms one can call it a light transmittance for the given order.

According to the "geometrical model" of the grating 100% efficiency (light transmittance) in m-order can be achieved if the direction of the blaze ray defined by the refraction at the blaze coincides with the direction of m-order diffraction, (Carmiña Londoño and Peter P. Clack, Modeling diffraction efficiency effects when designing hybrid diffractive lens systems, Appl. Opt. 31, 2248–2252 (1992)). It simply means that blaze material thickness is selected to direct the blaze ray along the m-order diffraction produced by the blaze zone spacing for the design wavelength of light.

The "geometrical model" provides a simple explanation of the diffractive lens structure which is important in a description of the present invention instead of relying on the mathematics of phase function, transmission function and its Fourier series to calculate diffraction efficiencies and solving the diffraction integral for intensity distribution.

For instance, if the blaze ray is refracted along the middle direction between zero- and (−1)-order, then the diffraction efficiency is equally split between zero- and $-1^{st}$-orders and the resulted blaze height is half of the one required for 100% efficiency at (−1)-order. Still one has to go through the formal process of calculation to determine that the efficiency of (−1)- and zero-order each equals to 40.5% for the design wavelength for the corresponding diffractive lens structure and the rest of light directed along higher orders of diffraction. In terms of the terminology, one can state that light transmittance to zero and (−1) diffraction order each equals 40.5%.

Choosing the appropriate blaze spacing ($r_j$) and blaze material thickness ($h_m$) as set forth hereinbelow, one can produce diffractive lens of the appropriate focal length ($f_m$) required by the ophthalmic lens application.

In a simple paraxial form the circular grating zones, also called echelettes or surface-relieve profile or grooves, can be expressed by the formula $r_j^2 = jm\lambda f$, i.e. the focal length of m-order diffraction (m=0, ±1, ±2, etc) for the design wavelength ($\lambda$) can be closely approximated by the following formula:

$$f_m = \frac{r_j^2}{jm\lambda} \quad (1)$$

In the paraxial approximation the blaze material thickness to produce 100% efficiency at m-order is $$h_m = \frac{m\lambda}{(n-n')} \quad (2)$$

where n=refractive index of the lens material and n'=refractive index of the surrounding medium.

Diffractive lens with 100% efficiency, i.e. all light is directed along the selected diffraction order is called Kinoform lens. (J A Jordan et al. Kinoform lenses, Appl. Opt. 9, 1883–1887, (1970))

A diffractive surface may be formed by different shapes of the periodic diffractive structure and not only by specific blaze shape and for the generality of this invention the term "groove" is used as the description of the variety of shapes of the diffractive structure.

U.S. Pat. No. 5,096,285 by Silberman describes diffraction surface with 100% efficiency to provide single diffraction power and the invention does not utilize the main advantage of the diffractive optic to use several diffraction orders (zero and −1, or +1 and −1, etc.) to reduce pupil dependency of the bifocal ophthalmic lens performance.

U.S. Appl. No. 20050057720 by Morris describes also diffractive 100% efficiency surface with the utilization of multiorder diffractive surface (MOD), i.e. the zones having boundary condition of phase shift by the multiple wavelength to provide similar diffraction efficiency for the range of wavelengths instead of only for the design wavelength.

Cohen and Freeman are the principal inventors of ophthalmic multifocal diffractive optic that utilizes several diffractive orders to form image from the objects at different distances. The Cohen patents: U.S. Pat. Nos. 4,210,391; 4,338,005; 4,340,283; 4,881,805; 4,995,714; 4,995,715; 5,054,905; 5,056,908; 5,117,306; 5,120,120; 5,121,979; 5,121,980 and 5,144,483. The Freeman patents: U.S. Pat. Nos. 4,637,697; 4,641,934; 4,642,112; 4,655,565, 5,296,881 and 5,748,28 where the U.S. Pat. No. 4,637,697 references to the blaze as well as step-shapes (binary) diffractive surface.

Other patents on diffractive lenses have been granted to Futhey: U.S. Pat. Nos. 4,830,481, 4,936,666, 5,129,718 and 5,229,797; Taboury: U.S. Pat. No. 5,104,212; Isaacson: U.S. Pat. No. 5,152,788; Simpson: U.S. Pat. Nos. 5,076,684 and 5,116,111 and Fiala: U.S. Pat. Nos. 6,120,148 and 6,536, 899.

Swanson in U.S. Pat. No. 5,344,447 describes tri-focal lens using binary type diffractive surface profile. Kosoburd in U.S. Pat. No. 5,760,871 also describes tri-focal lens with blaze and binary profiles.

Several patents describe the variable step size between the adjacent zones of the diffractive structure to control light transmittance at different diffraction orders with pupil size: U.S. Pat. Nos. 4,881,805 and 5,054,905 by Cohen describe so called progressive intensity bifocal lens where the step size at the adjacent zones reduced towards periphery to shift larger portion of light towards zero-order (far focus) diffraction image, i.e. to control light transmittance to the given order with pupil diameter. Baude at al in U.S. Pat. No. 5,114,220 discloses an ophthalmic lens which characteristically comprises at least two concentric regions having diffractive components with different phase profiles in order to use different orders of diffraction. Lee at al in U.S. Pat. No. 5,699,142 incorporates a similar concept into so called apodized lens by recommending the specific reduction in echelettes heights, so called apodization the diffractive surface echelettes heights, to split light initially equally between Far and Near foci (40.5% efficiency for each) and them the heights reduce towards lens periphery to shift larger portion of light towards far focus with larger pupil size, i.e. to control light transmittance with pupil diameter. Freeman in U.S. Pat. No. 5,748,282 also refers to the variable step size to control light intensity between different orders with pupil size variation.

U.S. Pat. No. 5,056,908 discloses an ophthalmic contact lens with a phase plate and a pure refractive portion within its optic zone that is placed at the periphery of phase zone area. U.S. Pat. No. 5,089,023 by Swanson also describes the lens with a combination of single focus refractive and diffractive segments that can be of bifocal design. In both inventions the refractive portion coincides with one of the diffractive order either for distant or near vision.

Thus, the diffractive optic offers the advantage to perform independently to pupil diameter. Common to all designs of the quoted patents is the fact that a bifocal diffractive lens is lacking intermediate vision. It has been shown that bifocal diffractive lens demonstrates two distinct intensities at two foci for distant and near vision (Golub M A, et al, Computer generated diffractive multi-focal lens. J. Modern Opt., 39, 1245–1251 (1992), Simpson M J. Diffractive multifocal intraocular lens image quality. Appl. Optics, 31, 3621–3626 (1992) and Fiala W and Pingitzer J. Analytical approach to diffractive multifocal lenses. Eur. Phys. J. AP 9, 227–234 (2000)). A presence of some intermediate vision reported clinically can be attributed to the aberrations of the ocular system of a given subject and not to the lens design itself.

The objective of the present invention is to provide the multifocal diffractive lens with the ability to offer a continuous focus covering far, intermediate and near vision. This would provide a naturally occurred vision similar to one through a pin-hole where a person can observe objects continually from far to near distances but without necessity to have small pupil (pin-hole) and, as a result, a very limited amount of light reaching the retina. The expectation of the lens performance according to the present invention is that the characteristic of the images of the objects at all distances from far to near are naturally occurred (pin-hole, for instance) and would inhibit a minimum of ghosting and halos commonly observed with present types of diffractive and refractive multifocal ophthalmic lenses.

SUMMARY OF THE INVENTION

A lens in accordance with the present invention includes a central aspherical zone of the variable power to provide the range of powers or several discrete refractive powers. This central refractive zone is preferably substantially smaller than a normal pupil diameter and may be about 1.25 to 2.5 mm in diameter.

The central zone is surrounded by an annular zone of bifocal diffractive power to provide far and near foci. The diffractive annulus is characterized by a plurality of annular zones of different structure to utilize 0- and (−1)-orders or (+1)- and (−1)-orders, etc.

For instance, the diffractive annulus may be designed with a gradual or step reduction of the proportion of light energy going to near with the increasing distance from the lens center. This can be accomplished by gradually reducing the step height of the diffractive structure from inside the annulus to a periphery thereof. For instance, the initial split ratio of light may be 1.5:1.0 for near to far foci with the light split ratio reducing to 0.1:1.0 for near to far foci at the diffractive annulus periphery. A specific rate of the light split change across the diffractive annulus may vary to suit specific design requirements. A typical diffractive annulus is between about 1.25–2.5 mm inside diameter to about 3 to 5 mm outside diameter.

The central aspherical zone may be placed on the same surface with diffractive bifocal annulus or on different surfaces of the lens. An arrangement with a aspherical zone on an anterior surface with a diffractive bifocal zone on a posterior surface may be particularly suitable for contact lenses. In this instance, the diffractive bifocal surface faces a cornea in order to keep it immersed in a tear post-lens film.

The diffractive bifocal annular zone may not abut the central aspherical zone. For instance, single focus diffractive or refractive zone corresponding to a single power can be placed inbetween the aspherical central zone and the diffractive bifocal annular zone. The diffractive single power zone may of multiorder diffractive surface (MOD), construction or commonly used single-order construction. The single power of this zone may be of any power but preferably of near power to compliment far dominant power of the central aspherical zone.

A method of designing an aspherical diffractive multifocal lens with a diffractive, multifocal annular zone in accordance with the present invention includes:

a) selecting a base curve defining far (distant) focus;

b) calculating the position of grooves located at radii $r_i$, for the base curve to produce near focus;

c) establishing a size of a central aspherical zone and corresponding aspherization to produce a range of foci around far focus; and d) selecting a step height for grooves within the diffractive annular zone to create a balance of light between far and near foci that complements contribution of central aspherical zone. The selection may include a zone with single near power and a zone with a function of the variation of grooves height to provide specific changes in the light split between far and near powers, i.e. difference "transmittance" for each power with the distance from the lens center.

Another method of designing an aspherical diffractive multifocal lens with a diffractive, multifocal annular zone utilizing both surfacesin accordance with the present invention includes:

a) selecting a base curve defining far (distant) focus;

b) calculating a position of grooves located at radii $r_i$, for the base curve to produce near focus on one of the lens surfaces;

c) establishing a size of the central aspherical zone and its corresponding aspherization on the other lens surface to produce a range of foci around far focus;

d) limiting an internal diameter of the diffractive annular zone to a external diameter of the central aspherical zone; and e) selecting a step height for the grooves within the diffractive annular zone to create a balance of light between far and near foci that complements contribution of central aspherical zone. This selection may include a zone with single near power and a zone with a function of the variation of grooves height to provide specific changes in the light split between far and near powers.

The peripheral zone outside diffractive bifocal annulus is primarily for far vision but can be aspherical one to compensate for the aberration arising at the eye periphery or to provide additional intermediate performance to compliment central aspherical and diffractive annulus areas. The peripheral zone may be placed on the same surface with the diffractive annular zone or on different surfaces of the lens. It may be advantageous to place the peripheral aspherical zone on a front surface with diffractive bifocal surface placed on a back surface of the lens which is particularly useful in case of contact lenses.

Another option of the diffractive bifocal surface provides increasing groove heights toward a selected zone diameter within the diffractive annular zone in order that more light is directed to far focus and less light to near focus until more light is directed to near. Then groove heights reduce a directing more light to far again until reaching the periphery of the diffractive annular zone. Then, there is always some near and far light at any area but the split between far and near varies—initially substantially small percentage towards Near then larger percentage toward Near and then again smaller percentage towards Near. The zone may be designed in the opposite progression—larger portion of light initially for Far, then smaller and then again larger portion for Far toward zone periphery.

The preferable design of the diffractive annular zone is to construct it into two subzones: the internal zone is diffractive single focus zone of near power, i.e. the grooves height is selected to direct light to near focus along, for instance, (−1)-order. The corresponding subzone (zone 2) behaves as the Kinoform producing 100% efficiency for near focus. The external diffractive subzone (zone 3) is constructed as a bifocal design, i.e. the groove heights are reducing from the height of the grooves at the zone 2 to direct larger fraction of light to near focus until the height reaches close to zero at the periphery of the zone 3 to direct most of the light to Far focus. The design might also be constructed with the internal zone 2 for near power being of refractive power of the surface curvature corresponding to Near power of the lens.

A grove profile may be linear, spherical, trigonometrical (cosine shape, for instance), or aspherical one. For instance, the groove profile of Zones 2 and 3 may follow the asphericity of Zone 4.

BRIEF DESCRITION OF THE FIGURES

Figure 3:
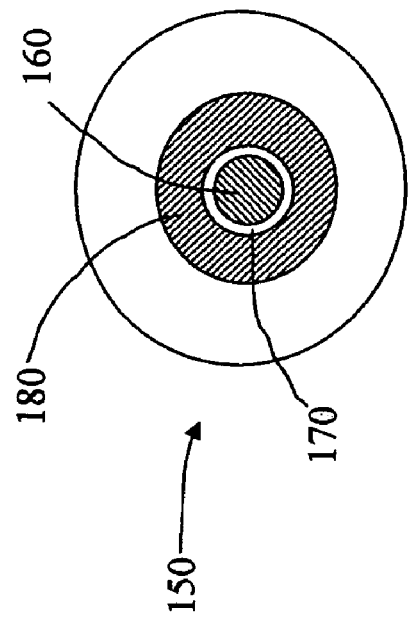
FIG. 3 is a plan view of a preferred embodiment of a lens made in accordance with the present invention which has diffractive bifocal zone spaced apart from of the central aspherical refractive zone.
Figure 7:
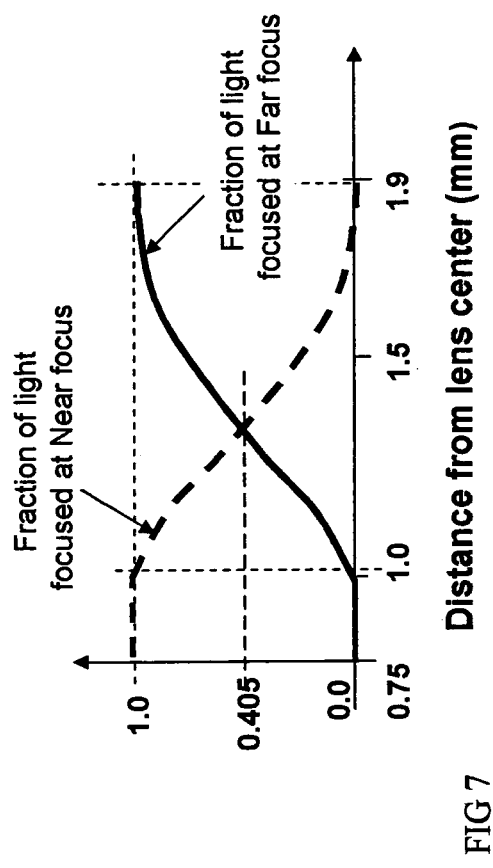

FIG. 7 demonstrates a preferred embodiment of aspherical diffractive lens transmittance that is divided into two zones: internal for Near power only and diffractive bifocal external zone for Far and Near powers;

FIG. 8A is a profile view of a preferred embodiment of the lens similar to one depicted on FIG. 3 with diffractive zones placed at an anterior surface;

FIG. 8B is a profile view of a preferred embodiment of the lens similar to one depicted on FIG. 3 with diffractive zones placed at a posterior surface;

FIGS. 9A and 9B are profile views of zone 2 and zone 3 similar to that shown in FIG. 8A with both zones being diffractive surface type.

Figure 11:
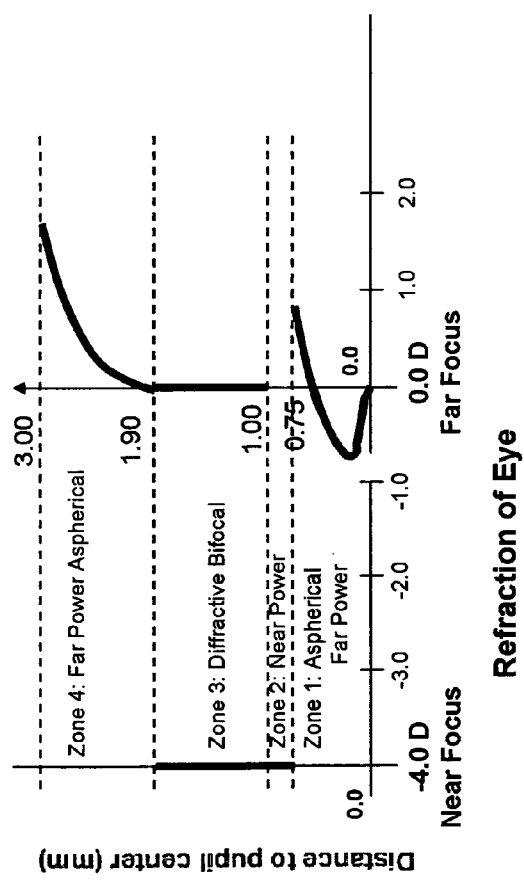
Figure 12:
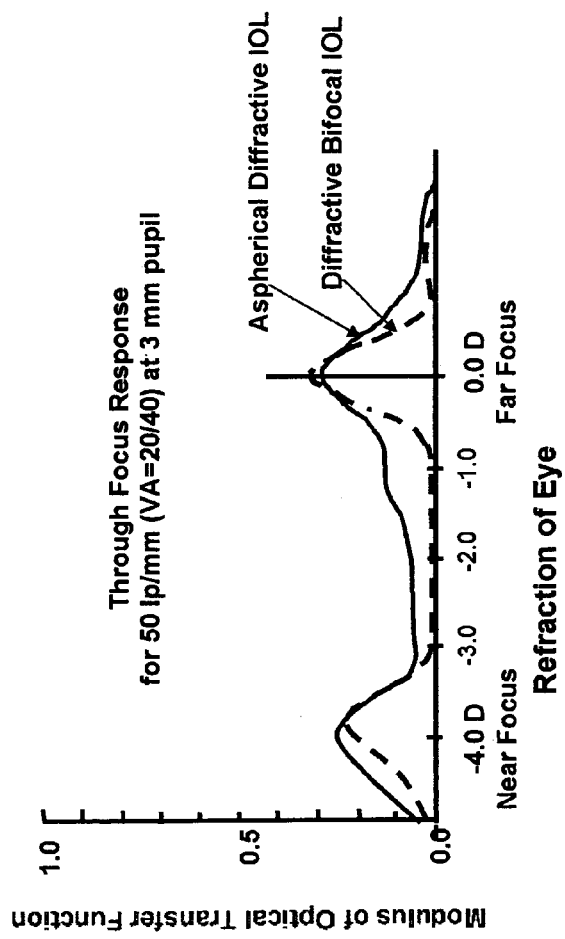

FIGS. 9C and 9D are profile views of the zone 2 and zone 3 similar to that shown in FIG. 8A with the internal zone being refractive type and external zone being diffractive bifocal surface;

FIG. 10 is a profile view of a preferred embodiment of a lens made in accordance with the present invention which has a base curve of a diffractive zone designed for near power;

FIG. 11 is a Power graph describing power of the rays across the pupil of the eye corresponding to a preferred embodiment of the aspherical diffractive multifocal lens in accordance with the present invention; and FIG. 12 is a graph representing image quality of the eye with preferred embodiment of the aspherical diffractive multifocal lens per the Power graph illustrated in FIG. 11.

DETAILED DESCRIPTION

Figure 1:
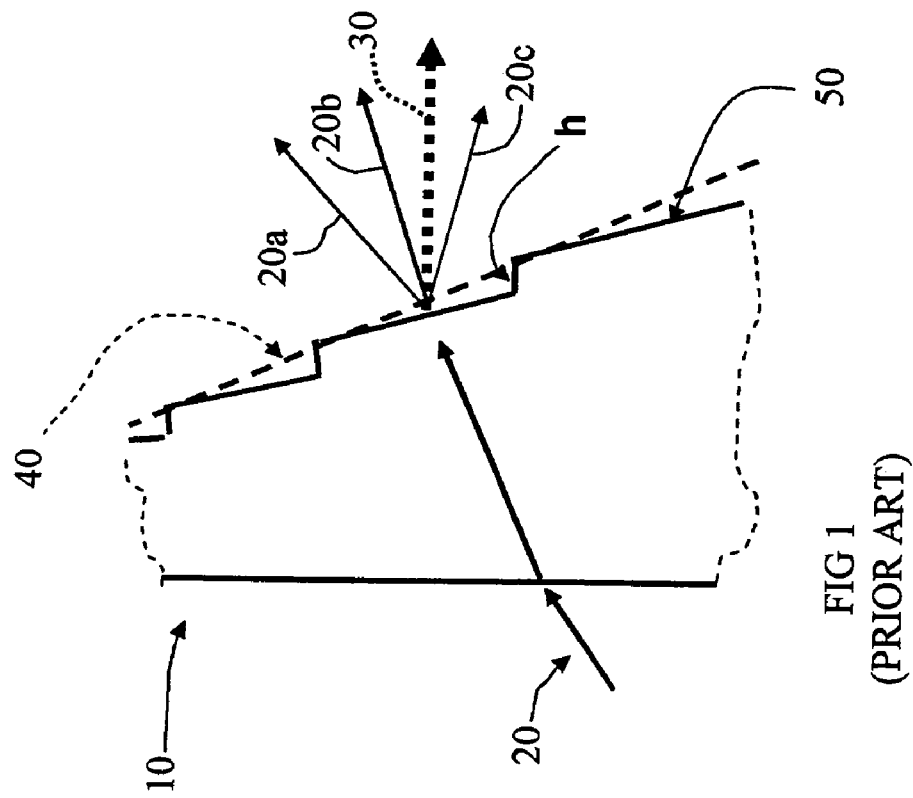
FIG. 1 illustrates a prior art diffractive lens with blazed periodic structure forming different diffraction orders along which the light can only be channeled. The figure also include a description of a "geometrical model" of the diffractive lens through the relationship between the blaze ray defined by the refraction at the blaze and directions of the diffraction orders.

FIG. 1 describes a portion of diffractive lens 10 with blazed periodic structure 50 creating different diffraction orders indicating by the directions 20a, 20b, 20c, etc. along which the light can only be channeled. The figure includes input light ray 20 refracted by the lens 10. It also shows the refractive base curve 40 that would refract the exiting ray corresponding to the input ray 20 along the direction of zero-order diffraction 20b. Direction of 1-order diffraction is shown by 20a and (−1)-order diffraction by 20c. Theoretically, there are infinite orders of diffraction.

The FIG. 1 incorporates a reference to the "geometrical model" of diffractive lens by including blaze ray 30 as the ray corresponding to the input ray 20 and refracted by the blaze. The direction of the blaze ray 30 differs from the direction of 0-order diffraction 20b due to the different refraction angles of the rays at the base curve 40 and blaze structure 50. The angle difference is created by the blaze material thickness (h).

If the blaze material thickness h is zero than the blaze structure 50 coincides with the base curve 40 and the lens becomes pure refractive type. If the blaze material thickness (h) increases to refract the blaze ray 30 along (−1)-order of diffraction 20b the lens becomes a Kinoform with 100% efficiency at (−1)-order diffraction. The blaze ray 30 at the FIG. 1 is placed in the middle between 0-order and (−1)-order diffraction to equally channel the light between these two orders. The rigorous diffraction theory demonstrates that maximum 40.5% of light can be channeled along each of these orders for the given design wavelength with the rest of the light is spread out between the higher orders of diffraction. In the present multifocal diffractive designs 0-order diffraction is selected to coincide with the power for Far vision (Far power) and (−1)-order coincides with the power required for Near vision (Near power).

Figure 2:
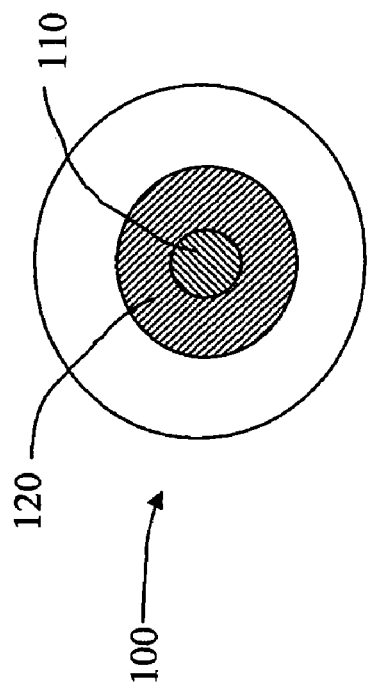
FIG. 2 is a plan view of a preferred embodiment of a lens made in accordance with the present invention which has diffractive bifocal zone abutting to the central aspherical refractive zone.

FIG. 2 is a plan view of a preferred embodiment of the ophthalmic lens 100 made in accordance with the present invention which has diffractive bifocal zone 120 abutting a central aspherical refractive zone 110. Both zones can be placed on the same lens surface or one on a lens posterior surface and another on anterior surface to create the demonstrated on the figure mutual zone arrangement. FIG. 2 demonstrates the central zone 110 with a spherical shape but other suitable shape may be utilized. For example, an annular shape may be located centrally to the diffractive bifocal zone 120. On the other hand, diffractive bifocal zone 120 may be spherical shape and not an annular type if placed on the surface other that the one where zone 110 is located but still with the diameter larger than the aspherical zone 110 to create the arrangement shown FIG. 2.

FIG. 3 is a plan view of another preferred embodiment of an ophthalmic lens 150 made in accordance with the present invention which has diffractive bifocal zone 180 placed outside of the central aspherical refractive zone 160 and not necessarily abutting therewith. Both zones can be placed on the same lens surface or one on the posterior and another on anterior surface to create the demonstrated mutual arrangement.

The zone 170 between diffractive bifocal zone 180 and central aspherical refractive zone 160 can be diffractive or refractive single power zone. It can be of annular type or spherical one if placed on the surface that is different from one where the aspherical refractive zone is located. The figure demonstrates central zone 160 to be of a spherical shape but for generality it may be of an annular shape located centrally to the diffractive bifocal zone 180.

Figure 4:
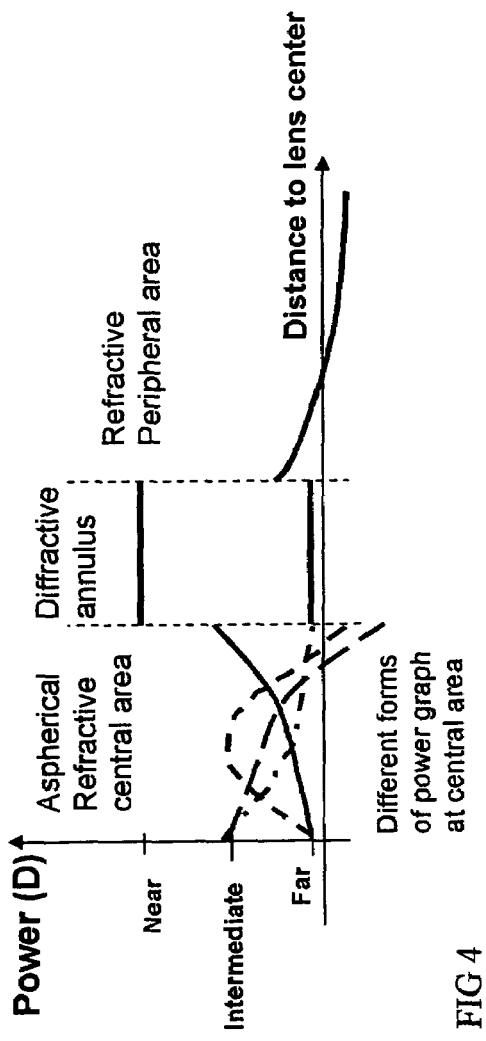
FIG. 4 is a Power graph of the lens described in the FIG. 2.

FIG. 4 demonstrates a Power graph of the lens described in the FIG. 2 where the power distribution along the central aspherical zone is represented of the variety of forms. For instance, the power can associate with far power at the center and then is raised to an intermediate level and than is reduced to or below far power level at the periphery of the zone, or the power of the zone may be of intermediate level at the center and then is reduced to the level below far power at the periphery of the zone. The diffractive annulus is represented by two power levels, one for far vision and another for near vision. The peripheral zone is shown as having a variable power that is reducing toward lens periphery. It is usually the case in the eyes with negative spherical aberration. The power curve may actually increases towards periphery if the lens is designed for the eye with positive spherical aberration.

Figure 5:
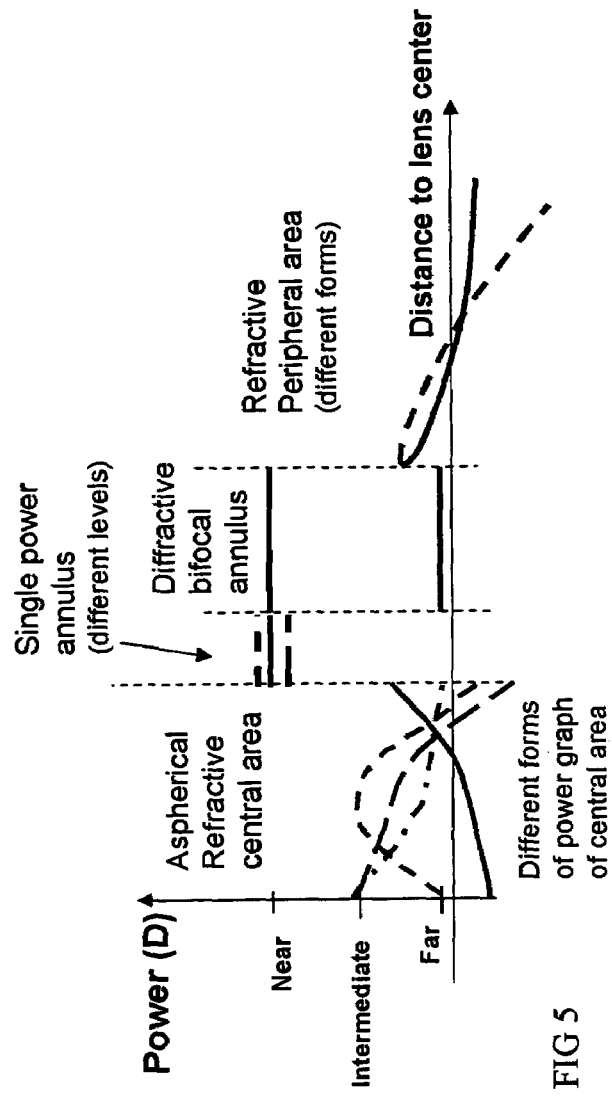
FIG. 5 is a Power graph of the lens described in the FIG. 3.

FIG. 5 is a Power graph of the lens described in the FIG. 3 where the power distribution along the central aspherical zone is also represented of the variety of forms. The difference from the FIG. 4 is the presence of the second single power zone between the central aspherical refractive zone and diffractive bifocal zone. The single power zone can be of any single power from far to near but preferably of near power to compliment far dominant power of the central aspherical refractive zone and can be created by refractive or diffractive type of surface. The diffractive bifocal annular zone and aspherical peripheral zone has been described in the FIG. 4 above and are of a similar nature.

Figure 6:
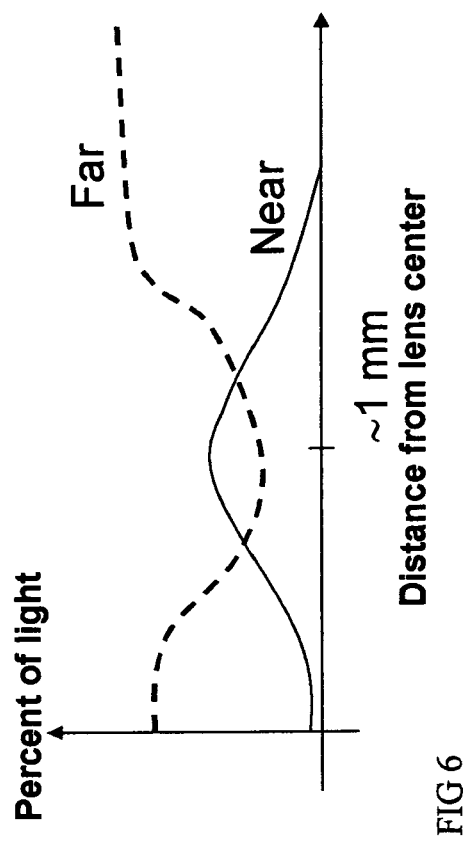
FIG. 6 shows graphs representing transmittance of light along the diffraction order associated with Far power and diffraction order associated with Near power that incorporates diffractive bifocal surface apodization of the grooves.

FIG. 6 describes the Transmittance graphs representing transmittance of light along the diffraction order associated with Far power and diffraction order associated with Near power in accordance to diffractive bifocal surface apodization of the grooves. By appropriately varying the groove heights, i.e. blaze material thickness in blaze type of diffractive surface, one can control the split of light between different diffractive orders.

As hereinabove noted, the groove profile can be linear, spherical, trigonometrical (cosine shape, for instance), or aspherical one. For instance, the groove profile of Zone 2 and 3 may follow the asphericity of Zone 4.

The graph covers the width of the bifocal diffractive lens. Assuming the base curve associates with far power, the Transmittance graphs demonstrate that at the internal side of the annular zone the groove height is very small in order to channel light primarily along the diffraction order associated with Far power, then the groove height increase to channel more light along the diffractive zone associated with Near power around 1 mm from the lens center and then the groove height reduces again to channel more light along the diffractive power associated with far power. In general, no apodization can be applied and the light is split constantly within the diffractive bifocal zone between the diffraction orders associated with far and near powers. The control in light split between far and near can be made in steps, i.e. each small portion of the zone has a constant groove height to control the split from one portion to another, i.e. the discrete apodization. In general, an apodization can be of variable form to meet desired performance objectives.

FIG. 7 provides an example of one of the preferable designs of the aspherical diffractive intra-ocular lenses. The design can be applied to contact lens by increasing the zone sizes by about 15% which corresponds to the relative scaling of the contact lens vs. intraocular lens due to the difference in their positions. The annular zone of radii between 0.75 mm and 1.0 mm is for near vision as 100% of light is transmitted to near focus. The diffractive bifocal zone occupies the width between 1.0 and 1.9 mm radii. In order to design the appropriate groove apodization one has to define a desirable transmittance to Far and Near foci.

The transmittance can be defined by a general form:

$$T=T_0\cdot(1-T_1\cdot r-T_2\cdot r^2-T_3\cdot r^3-T_4\cdot r^4) \quad (3)$$

The coefficients for this particular design are provided by Table 1.

TABLE 1

| Efficiency/Transmittance | $T_0$ | $T_1$ | $T_2$ | $T_3$ | $T_4$ |
|---|---|---|---|---|---|
| Far focus | 2.508375 | 3.010962 | −2.98324 | 1.074313 | −0.13188 |
| Near focus | −16.4189 | 3.593128 | −4.31017 | 2.167969 | −0.3942 |

Thus, the apodization of the grooves within the diffractive bifocal zone is such that it starts with height to direct all light along the diffraction order associated with near focus and then the heights are reduced to create the transmittance described by Table 1 until reaching close to zero to direct all light along the diffraction order associated with far focus.

FIG. 8A is a profile view of the preferred embodiment of the lens 150a similar to one depicted on FIG. 3 with diffractive zones placed on the anterior surface. The optical axis is shown by 190a. The parent conventional monofocal lens is a combination of anterior surface 200 acting as the base curve of the diffractive surface and posterior surface 250. For generality, the posterior surface 250 may be diffractive or refractive type. The anterior surface consists of 4 zones: central aspherical zone 210 designated as zone 1, next annular zone 220a of single power designated as zone 2, next annular diffractive bifocal zone 230b designated as zone 3 and aspherical peripheral zone 240 designated as zone 4. In order to provide a design specifics one can design 20 D lens with refractive index 1.494 with the following characteristics:

Base radius for Far power is 12.3 mm and posterior surface radius is 25.66 mm, 4 D Add for Near power corresponds to 9.32 mm radius.

Zone 1 is up to 1.5 mm diameter with vertex radius equals 11.2 mm corresponding to intermediate power and at least part of the zone manifests the surface shape defined by the aspherical form:

$$Z=\text{Sphere}(r=11.2\text{ mm})+A_4\cdot r^4 \quad (4)$$

with aspherical coefficient $A_4=-0.005387616$

For instance, within the range of 0.5 to 1.5 mm diameters.

Zone 4 within 3.8–6.0 mm diameters with vertex radius 12.3 mm and surface shape is defined by the aspherical form:

$$Z=\text{Sphere}(r=12.3\text{ mm})+B_2\cdot r^2+B_4\cdot r^4+B_6\cdot r^6+B_8\cdot r^8 \quad (5)$$

With aspherical coefficients $B_2=0.000227$; $B_4=-0.0001876$; $B_6=0.0000217668$; $B_8=-0.0000030947$ Bi-convex shape of lens 150a is shown as an example only and the design concept is fully applicable to other lens shapes such as meniscus or bi-concave one. The corresponding bi-convex or bi-concave lens can be of equal or non-equal curvatures for anterior and posterior surfaces.

FIG. 8B demonstrates a modification of the embodiment shown in FIG. 8A with a lens 155 having the both annular zones 2 and 3 referenced to as 220b and 230b or only zone 3 referenced to as 230b at the posterior lens surface.

FIG. 9A is a profile view of the portion of lens 150a with zone 2 of width $s_1$ and zone 3 of width $l_1$ and posterior surface 250. The width $s_1$ is about from 0.2 mm to 0.5 mm and width $l_1$ is about from 0.4 mm to 1.5 mm. The base curve 260 associates with far focus. Zone 2 is constructed as Kinoform to direct light to Near or Intermediate single focus with the groove height is closely defined by the Equation 2. Zone 3 is constructed to create bifocal diffractive surface to split the light between Far and Near foci. In this particular case the Zone 2 is described by grooves 300 of height $h_m$ to direct light to near focus. Zone 2 is constructed with groove height to direct light to near focus, groove height 310 is reduced to split light between far and near until all light is directed to far focus at the external periphery of the zone where the groove height is approaching zero. The figure demonstrates groove height that is continually reduced but in general they may be have the height reduction in steps, i.e. constant height within a small subzone width then another constant height within another small subzone width, etc. "Geometrical model" of the diffractive optic explains the reduction in grove height in order to direct the blaze ray in between the diffraction orders associated with far and near foci in order to split the light between these two orders though a rigorous diffraction theory is required to provide a fully quantitative solution for the groove heights meeting the specific transmittance requirements for far and near foci.

FIG. 9B is a profile view of zone 2 and zone 3 of lens 150b similar to those described by FIG. 9A with both zones being recessed by the depth 295 which is at least as deep as the groove height ($h_m$). This construction is particularly useful when involve soft material when the diffractive surface can be pressed against an ocular tissue and deform its shape. For instance, for placement at the posterior surface of the intraocular lens or contact lens that may interface with the ocular tissue and deform the groove shapes.

FIG. 9C is a profile view of zone 2 and zone 3 of lens 150c similar to those described by FIG. 9A but with Zone 2 being a single focus refractive type surface 265a to provide near or intermediate focus and Zone 3 being similar to one on FIG. 9A.

FIG. 9D is a profile view of zone 2 and zone 3 of lens 150d similar to those described by FIG. 9B but with Zone 2 being a single focus refractive surface 265a to provide near or intermediate focus and Zone 3 being similar to one on FIG. 9B that is recessed into the lens material to protect the grooves from a deformation if the surface is pressed against an ocular tissue.

FIG. 10 offers another variation of lens 150d to form the lens 150e with the diffraction bifocal zone having the base curve associated with near focus of the lens 150e, i.e. the direction of zero-order diffraction is towards Near focus. Far power of the diffractive multifocal lens in this case is created by first-order diffraction. In order to maintain similar to lens 150d performance, the groove height is initially close to zero to direct most of the light to near focus and then the groove height increases until reaching the height $h_m$ for all light to be directed towards far focus.

FIG. 11 is a Power graph describing powers of the rays across the pupil of the eye model corresponding to the preferred embodiment of the aspherical diffractive multifocal lens. To define the aspherical diffractive lens design that is independent to the lens placement (contact lens, intracorneal implant or intraocular lens) or lens material one can characterize the lens design in terms of image property. For instance, FIG. 11 characterizes the design in terms of the focus location for all rays passing through the aspherical diffractive multifocal lens, where each ray crosses the optical axis at certain location measured from the intended Far focus of the corresponding parent monofocal lens. For consistency, the pupil scale is taken at the intraocular lens plane and the eye model used is so called Lotmar model, Table 2.

TABLE 2

| Ocular element | Thickness (mm) | $\lambda$ = 0.546µ Refr. Index | Radius (mm) | Conic | Coeff on $r^4$ | Coeff on $r^6$ |
|---|---|---|---|---|---|---|
| CORNEA | 0.55 | 1.377 | 7.8 | −1 | 0.0001881 | −1.4e-006 |
| Back surface | | | 6.5 (spherical surface) | | | |
| AQUEOUS | 4.05 | 1.3375 | | | | |
| IRIS-PUPIL | 0.0 | | | | | |
| IOL | 0.8 | 1.494 | Aspherical Diffractive Surface | | | |
| Back surface | | | −25.66 (spherical surface) | | | |
| VITREOUS | 18.85 | 1.336 | | | | |
| RETINA-IMAGE | | | −12.0 (spherical surface) | | | |

For the above specified conditions, the preferred design of the central aspheric zone of the aspherical diffractive lens produces a relationship between each ray position and Power deviation from the Far Power defined by the following 3rd Order Polynomial:

$$y=a_1+b_1 \cdot x+c_1 \cdot x^2+d_1 x^3, \quad (6)$$

where y=distance to the center of the pupil: from zero to 0.75 mm,
x=Power deviation from Far power,
and the polynomial coefficients are:
$a_1$=0.5279; $b_1$=0.2512; $c_1$=0.0730; $d_1$=0.1141

The description corresponds to one created by the lens per FIG. 8A with the asphericity per Equation 4 within the diameter of 1.5 mm.

All rays focused at near focus for zone 2 within the diameters 1.50–2.0 mm.

The rays are split between Far and Near foci for zone 3 within the diameters 2.0–3.8 mm with the transmittance per apodization defined by FIG. 7.

The preferred performance of the peripheral aspheric zone 4 of aspherical diffractive multifocal lens is defined by the following 6th Order Polynomial:

$$y=a_4+b_4 \cdot x+c_4 \cdot x^2+d_4 x^3+e_4 \cdot x^4+f_4 x^5+g_4 x^6, \quad (7)$$

where y=distance to the center of the pupil: from 1.9 to 3.0 mm,
x=Power deviation from Far power,
and the polynomial coefficients are:
$a_4$=2.092; $b_4$=2.692; $c_4$=−7.9043; $d_4$=14.645;
$e_4$=−14.2524; $f_4$=6.7944; $g_4$=−1.25137

The description corresponds to one created by the lens per FIG. 8A with the asphericity per Equation 5 within the diameters 3.8–6.0 mm.

FIG. 12 demonstrates a TFR graph representing image quality of the eye with preferred embodiment of the aspherical diffractive multifocal lens per FIG. 11 and transmittance function of its apodized diffractive bifocal zone per FIG. 7. The resulted image quality is commonly defined by the Modulus of the Optical Transfer Function for different focus positions, so called Through Focus Response (TFR).

The TFR of the preferred aspherical diffractive lens is compared with TFR of the diffractive multifocal lens where light is equally split between far and near foci (40.5% at each for the design wavelength with the rest of light is distributed between higher diffraction orders) for 3 mm lens aperture. The graphs demonstrate the remarkable advantage of the preferable aspherical diffractive multifocal lens over the diffractive multifocal lens by manifesting Intermediate vision capability in addition to the comparable Near and Far vision capabilities.

What is claimed is:

1. A multifocal ophthalmic lens comprising:
a lens element having an anterior surface and a posterior surface;
a central aspherical refractive zone, providing a range of foci that includes far focus, disposed on one of the anterior and posterior surfaces; and
a diffractive bifocal zone disposed outside of the aspherical refractive zone.

2. The lens according to claim 1 wherein said diffractive bifocal zone is an annulus.

3. The lens according to claim 1 wherein the refractive zone and the diffractive zone abut one another.

4. The lens according to claim 1 wherein the refractive zone and the diffractive zone are spaced apart from one another.

5. The lens according to claim 4 further comprising a single power zone disposed between the central aspherical refractive zone and the diffractive bifocal zone, the single power zone being one of a single power diffractive zone and a single power refractive zone.

6. The lens according to claim 1 wherein each of the central refractive zone and the diffractive bifocal zone have constant radii.

7. The lens according to claim 1 wherein each of the central refractive zone and the diffraction bifocal zone have varying radii.

8. The lens according to claim 1 wherein said diffractive bifocal zone comprises a plurality of grooves, the grooves being apodized from a height directing light along a diffractive order associated with near focus to a height directing light along a diffractive order associated with far focus.

9. The lens according to claim 8 wherein a groove profile is selected from a group consisting of linear, spherical, trigonometric, aspherical profiles.

10. The lens according to claim 1 wherein the diffractive bifocal zone is recessed into one of the anterior and posterior surfaces.

11. The lens according to claim 1 wherein said lens element is an intraocular lens.

12. The lens according to claim 1 wherein said lens element is a contact lens.

13. The lens according to claim 1 wherein said lens element is an artificial cornea.

14. The lens according to claim 1 wherein said lens is a lamellar implant.

15. A multifocal ophthalmic lens comprising:
  a lens element having an anterior surface and a posterior surface;
  a central aspherical refractive zone, providing a range of powers that includes distance vision, disposed on said anterior surface and centered on a transverse axis; and
  a diffractive bifocal zone disposed on said posterior surface and centered on the transverse axis.

16. The lens according to claim 15 wherein said diffractive bifocal zone is an annulus.

17. The lens according to claim 16 wherein the refractive zone and the diffractive zone abut one another wherein viewed along the transverse axis.

18. The lens according to claim 16 wherein the refractive zone and the diffractive zone are spaced apart from one another when viewed along the transverse axis.

19. The lens according to claim 18 further comprising a single power zone disposed on said posterior surface and between the central aspherical refractive zone and the diffractive bifocal zone wherein viewed along the transverse axis.

20. The lens according to claim 15 wherein each of the centered refractive zone and the diffractive bifocal zone have constant radii.

21. The lens according ot claim 15 wherein each of the central refractive zone and the diffractive bifocal zone have varying radii.

22. The lens according to claim 15 wherein said diffractive bifocal zone comprises a plurality of grooves, the grooves being apodized from a height directing light along a diffractive order associated with new focus to a height directing light along a diffractive order associated with far focus.

23. The lens according to claim 22 wherein a groove profile is selecting from a group consisting of linear, spherical trigonometric and aspheric profiles.

24. The lens according to claim 15 wherein said lens element is an intraocular lens.

25. The lens according to claim 15 wherein said lens element is a contact lens.

26. The lens according to claim 15 wherein said lens element is an artificial cornea.

27. The lens according to claim 15 wherein said lens is an lamellar implant.

28. A method of designing an aspherical diffractive multifocal surface with a diffractive, multifocal annular zone comprising:
  a) selecting a base curve defining far (distant) focus;
  b) calculating the position of grooves located at radii $r_i$, for the base curve to produce near focus;
  c) establishing a size of a central aspherical zone and corresponding aspherization to produce a range of foci around far focus; and
  d) selecting a step height for grooves within the diffractive annular zone to create a balance of light between far and near foci that complements contribution of central aspherical zone.

29. A method of designing an aspherical diffractive multifocal lens with a diffractive, multifocal annular zone utilizing anterior and posterior surfaces comprising:
  a) selecting a base curve defining far (distant) focus;
  b) calculating a position of grooves located at radii $r_i$, for the base curve to produce near focus on one of the lens surfaces;
  c) establishing a size of the central aspherical zone and its corresponding aspherization on the other lens surface to produce a range of foci around far focus;
  d) limiting an internal diameter of the diffractive annular zone to a external diameter of the central aspherical zone; and
  e) selecting a step height for the grooves within the diffractive annular zone to create a balance of light between far and near foci that complements contribution of central aspherical zone.

30. A multifocal ophthalmic lens comprising:
  a lens element having an anterior surface and a posterior surface;
  a central aspherical refractive zone, providing several discrete refractive powers, disposed on one of the anterior and posterior surfaces; and
  a diffractive bifocal zone disposed outside of the aspherical refractive zone.

31. A multifocal ophthalmic lens comprising:
  a lens element having an anterior surface and a posterior surface;
  a central aspherical refractive zone, providing a range of powers, disposed on one of the anterior and posterior surfaces; and
  a diffractive bifocal zone disposed outside of the aspherical refractive zone.

* * * * *